United States Patent
Atwal et al.

(10) Patent No.: US 6,262,122 B1
(45) Date of Patent: Jul. 17, 2001

(54) ENANTIOMERS OF 4-[[(CYANOIMINO) [(1,2,2-TRIMETHYLPROPYL)AMINO]METHYL]AMINO]BENZONITRILE

(75) Inventors: Karnail S. Atwal, Newtown, PA (US); Joyce Chou, Monmouth Junction, NJ (US); Seshadri Neervannan, Thousand Oaks, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/615,345

(22) Filed: Jul. 12, 2000

Related U.S. Application Data

(63) Continuation of application No. 09/447,002, filed on Nov. 22, 1999, which is a continuation of application No. 09/119,884, filed on Jul. 21, 1998, now Pat. No. 6,013,668.
(60) Provisional application No. 60/055,568, filed on Aug. 13, 1997, and provisional application No. 60/071,364, filed on Jan. 15, 1998.

(51) Int. Cl.[7] .......................... A61K 31/16; C07C 279/18
(52) U.S. Cl. ................................ 514/609; 564/104
(58) Field of Search .............................. 564/104; 514/609

(56) References Cited

U.S. PATENT DOCUMENTS

| | | |
|---|---|---|
| H1480 * | 9/1995 | Luo ........................................ 424/400 |
| 4,057,636 | 11/1977 | Petersen . |
| 4,139,619 | 2/1979 | Chidsey, III . |
| 4,596,812 | 6/1986 | Chidsey, III et al. . |
| 5,011,837 * | 4/1991 | Atwal et al. ........................ 514/227.8 |
| 5,244,664 | 9/1993 | Godtfredsen . |
| 5,578,599 | 11/1996 | Diani et al. . |

FOREIGN PATENT DOCUMENTS

| | | |
|---|---|---|
| 392802A2 | 10/1990 | (EP) . |
| 2740331 * | 4/1997 | (FR) . |
| WO92/09259 | 6/1992 | (WO) . |

OTHER PUBLICATIONS

Meisheri, K.D. et al, "Enzymatic and Non–Enzymatic Sulfation Mechanisms in the Biological Actions of Minoxidil", Biochemical Pharmacology, vol. 45, No. 2 pp. 271–279, 1993.

Buhl, A.E. et al, "Potassium Channel Conductance: A Mechanism Affecting Hair Growth both In Vitgro and In Vivo", J. Invest. Dermatol., vol. 98, No. 3, pp. 315–319, Mar. 1992.

Pettinger, W.A. et al, "Side Efects of Vasodilator Therapy", Suppl. II Hypertension, vol. 11, No. 3, pp. II–34–II–36, Mar. 1998.

* cited by examiner

Primary Examiner—Floyd D. Higel
Assistant Examiner—Ebenezer Sackey
(74) Attorney, Agent, or Firm—Burton Rodney

(57) ABSTRACT

The (R)-enantiomer of 4-[[(cyanoimino)-[(1,2,2-trimethylpropyl)amino]methyl]amino]-benzonitrile as well as the corresponding (S)-enantiomer are useful for promoting hair growth such as in male pattern baldness.

23 Claims, 1 Drawing Sheet

Figure 1:
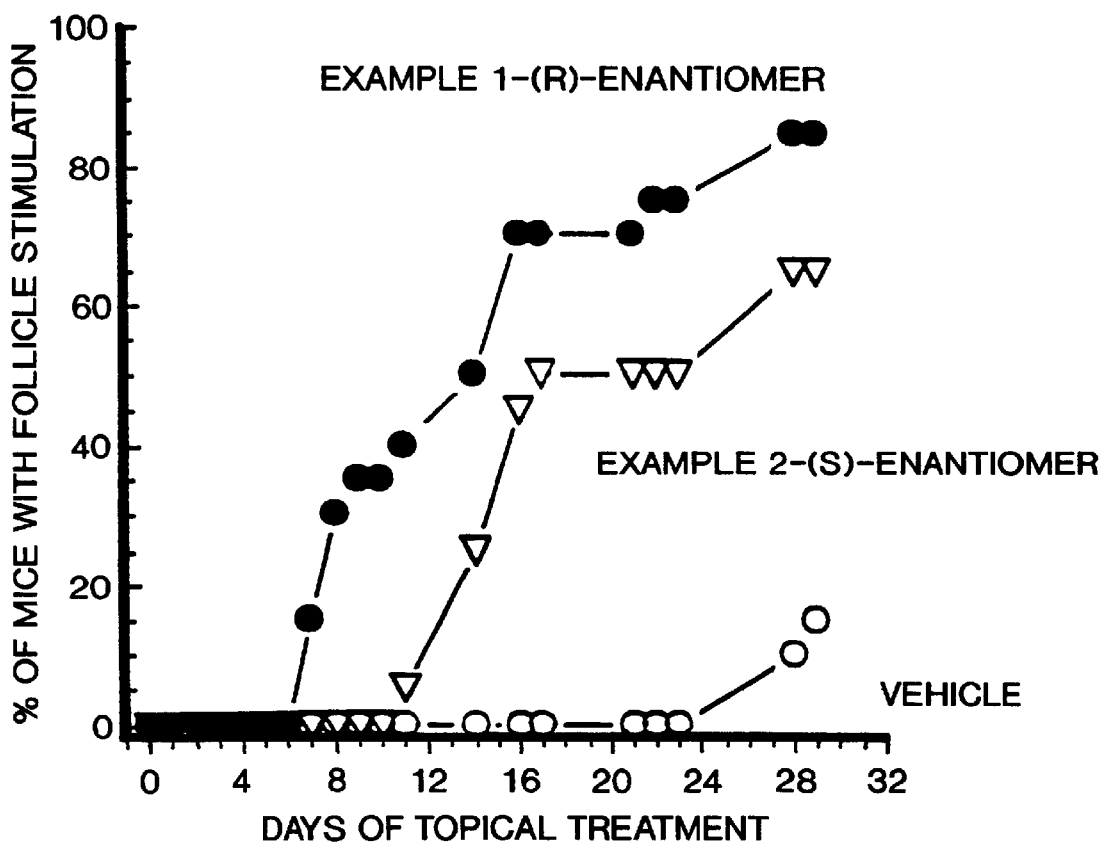

ENANTIOMERS OF 4-[[(CYANOIMINO) [(1,2,2-TRIMETHYLPROPYL)AMINO]METHYL]AMINO]BENZONITRILE

This application is a continuation of Ser. No. 09/447,002 filed Nov. 22, 1999 which is a continuation of Ser. No. 09/119,884 filed Jul. 21, 1998 now U.S. Pat. No. 6,013,668 which claims benefit of 60/055,568 filed Aug. 13, 1997 which claims benefit of 60/071,364 filed Jan. 15, 1998.

FIELD OF THE INVENTION

The present invention relates to the (R)- and (S)-enantiomers of 4-[[(cyanoimino)[(1,2,2-trimethyl-propyl)amino]methyl]amino]benzonitrile, pharmaceutical compositions containing same, and a method for promoting hair growth employing such enantiomers.

BACKGROUND OF THE INVENTION

Potassium channel openers such as minoxidil (Upjohn), pinacidil (Lilly) and diazoxide (Shiseido and Schering-Plough) are known for their hair growth stimulating activity. Thus, U.S. Pat. Nos. 4,596,812 and 4,139,619 disclose use of minoxidil in the treatment of male pattern baldness, alopecia areata and balding in females. U.S. Pat. No. 4,057,636 discloses pinacidil. DE 3,827,467A discloses combinations of minoxidil and hydrocortisone or retinoids.

U.S. Pat. No. 5,011,837 to Atwal et al discloses aryl cyanoguanidines which possess potassium channel activating activity and are useful therapy for hypertension and other cardiovascular disorders, for various central nervous system disorders, kidney and urinary problems as well as for the promotion of hair growth, for example in the treatment of male pattern baldness (alopecia). These aryl cyanoguanidines have the structure

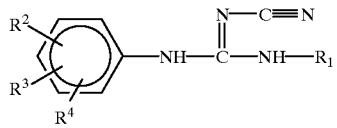

Ia and its possible tautomers

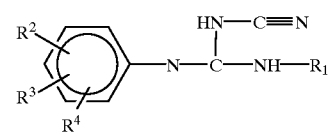

Ib and

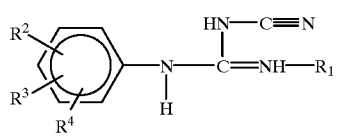

Ic including pharmaceutically acceptable salts, wherein $R_1$ is alkyl, alkenyl, alkynyl, haloalkyl, cycloalkyl, aryl, arylalkyl or cycloalkylalkyl;

$R_2$ is

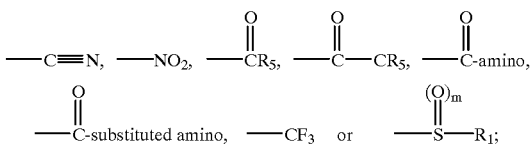

$R_3$ and $R_4$ are each independently selected form —$R_2$, hydrogen, alkyl, alkenyl, alkynyl, haloalkyl, halo, alkoxy, —NHalkyl, —N—(alkyl)$_2$, —S-alkyl, —O-aryl-alkyl, —S—arylalkyl or —S-aryl, —O-aryl, —NHaryl-alkyl, or $R_2$ and $R_3$ taken together are a group which form a ring with the two carbon atoms to which they are attached, which group is selected from

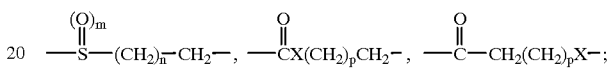

wherein m=1 or 2, n=3–5, p=2–4,

X is O, NR$_5$, CH$_2$; and

R$_5$ is hydrogen or R$_1$.

Example 1 of U.S. Pat. No. 5,011,837 discloses the preparation of 4-[[(cyanoimino)-[(1,2,2-trimethylpropyl)amino]benzonitrile

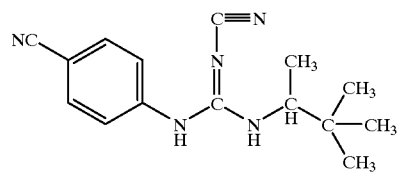

in the form of its racemic mixture.

PCT Application WO 92/02225 discloses a combination of a potassium channel opener and a 5-α-reductase inhibitor for promoting hair growth.

PCT Application WO 92/09259A discloses use of an androgen blocker and a potassium channel activator for stimulation of hair growth.

DESCRIPTION OF THE INVENTION

In accordance with the present invention, it has been unexpectedly found that the (R)-enantiomer of 4-[[(cyanoimino)[(1,2,2-trimethylpropyl)amino]-methyl]amino]benzonitrile, including pharmaceutically acceptable salts, thereof exhibits remarkable hair growth promoting activity which is superior in such regard to the corresponding (S)-enantiomer and the racemic mixture of such enantiomers. In fact, it has been found that the (R)-enantiomer is surprisingly and unexpectedly more effective in stimulating hair follicles to produce hair growth at a substantially faster rate as compared to the corresponding (S)-enantiomer.

The above (R)-enantiomer of the invention has the structure I

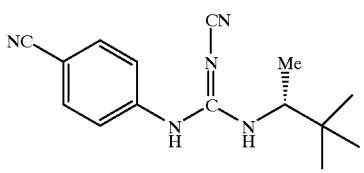

I

The (R)-enantiomer I will be in substantially pure form, that is, will be at least 99% pure (R)-enantiomer and will at most contain 1% (S)-enantiomer.

In addition, in accordance with the present invention, it has been found that the (S)-enantiomer of 4-[[(cyanoimino)[(1,2,2-trimethyl-propyl)amino]methyl]amino]benzonitrile, including pharmaceutically acceptable salts thereof, exhibits excellent hair growth promoting activity.

The above (S)-enantiomer of the invention has the structure II

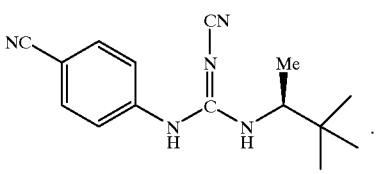

II

The (S)-enantiomer II will be in substantially pure form, that is, will be at least 99% pure (S)-enantiomer and will at most contain 1% (R)-enantiomer.

The enantiomers of the invention form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, and the like. The salts are obtained by reacting the product with an equivalent amount of the acid in a medium in which the salt precipitates.

The present invention also includes pharmaceutical compositions containing the (R)-enantiomer of 4-[[(cyanoimino)[(1,2,2-trimethyl-propyl)amino]methyl]amino]benzonitrile or a pharmaceutically acceptable salt thereof and a pharmaceutically acceptable carrier therefor.

In addition, the present invention also includes pharmaceutical compositions containing the (S)-enantiomer of 4-[[(cyanoimino)[(1,2,2-trimethylpropyl)amino]methyl]amino]benzonitrile or a pharmaceutically acceptable salt thereof and a pharmaceutically acceptable carrier therefor.

The (R)-enantiomer of the invention, that is, (R)-4-[[(cyanoimino)[(1,2,2-trimethylpropyl)-amino]methyl]amino]benzonitrile may be prepared according to the following reaction sequence:

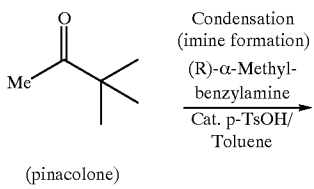

(pinacolone)

Condensation
(imine formation)
(R)-α-Methyl-
benzylamine
Cat. p-TsOH/
Toluene

-continued

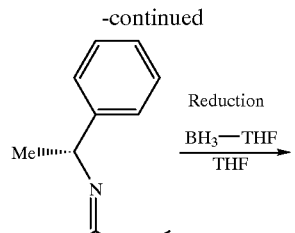

Reduction
$\xrightarrow{BH_3-THF}{THF}$

1

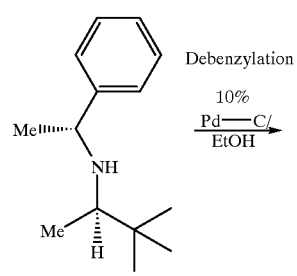

Debenzylation
$\xrightarrow{10\% \; Pd-C/}{EtOH}$

2

Coupling Reaction

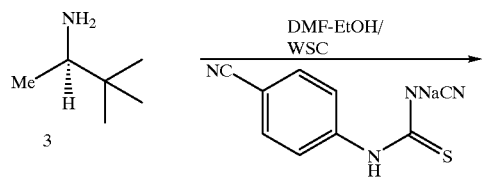

DMF-EtOH/
WSC

3

(prepared as described in Example 1 Part A of U.S. Pat. No. 5,011,837)

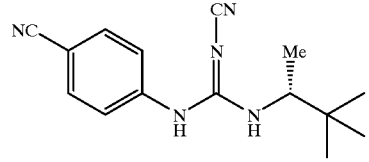

(R)-enantiomer

I

The (S)-enantiomer of the invention, that is (S)-4-[(cyanoimino)[(1,2,2-trimethylpropyl)-amino]methyl] amino]benzonitrile may be prepared according to the above reaction sequence for preparation of the (R)-enantiomer except that (S)-α-methylbenzylamine is employed in place of (R)-α-methylbenzylamine to eventually form

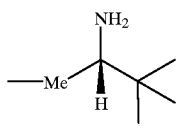

which is reacted with the 4-cyano-N'-(4-cyanophenyl) thiourea, monosodium salt to form the (S)-enantiomer (II).

The (R)-enantiomer I of the invention or the (S)-enantiomer II of the invention may be formulation with other hair growth promoting compounds such as the potassium channel openers minoxidil (Upjohn) and/or diazoxide (Shiseido and Schering-Plough), as well as cromakalim and pinacidil; a 5-α-reductase inhibitor such as finasteride (Merck's Proscar®), terazosin HCl (Abbott's Hytrin®), or doxaosin mesylate (Pfizer's Cardura®); and/or an androgen blocker such as 4-(5-methoxyheptyl)-hexahydro-2(1H)-pentalenone as disclosed in PCT Application WO 92/09259A, vasoconstrictors such as betamethasone dipropionate, corticosteroids such as hydrocortisone, and scopolamine, and cyproterone acetate.

The enantiomers of the invention may be administered via topical, oral, parenteral or rectal routes as described in U.S. Pat. No. 5,011,837 (incorporated herein by reference), with topical being preferred. Thus, the enantiomers of the invention in suitable topical formulations are applied to the skin region where hair growth is desired.

Typical topical formulations for use herein will include conventional ointments, creams, lotions, waxes, gels, pastes, jellies, sprays, aerosols and the like in aqueous or non-aqueous formulations. Examples of suitable topical formulations are disclosed in U.S. Pat. Nos. 4,139,619 and 4,596,812 which are incorporated herein by reference.

The enantiomers of the invention will be used in an effective amount, that is, in an amount sufficient to promote hair growth or treat hair growth disorders, such that hair growth is increased or produced. A typical topical composition will include from about 0.01 to about 15% by weight, preferably from about 0.1 to about 10% by weight of the composition.

The topical formulations containing the enantiomers of the invention can be applied to the area to be treated such as the scalp in humans, by spraying, dabbing or swabbing to deliver the enantiomer to the region of the hair follicle. The formulations will be applied to the area of treatment on a routine basis prior to, during and subsequent to hair growth, at least once daily, and preferably two or more times daily.

The accompanying Figure is a graph showing the effect of a once daily application of each of the (R)- and (S)-enantiomers described herein on hair growth in male C3H mice.

The following Examples represent preferred embodiments of the present invention.

EXAMPLE 1

(R)-4-[[(Cyanoimino)[(1,2,2-trimethylpropyl) amino]-methyl]amino]benzonitrile

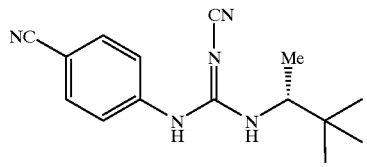

A. (R)-1,2,2-Trimethylpropyl amine

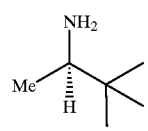

The title compound was prepared according to the procedure described by Manley and Quast (*J. Med. Chem.* 1992, 35, 2327–2340) with some modification. A mixture of pinacolone (29 g, 290 mmol), (R)-α-methylbenzyl amine (17.6 g, 145 mmol) and p-toluenesulfonic acid monohydrate (300 mg) in toluene (150 mL) was refluxed using a Dean-Stark trap (to remove water from the reaction mixture) for 3 days. The solvent was evaporated and the residue was distilled at ca. 120–2° C. (9 mm) to give 21 g (71% yield) of

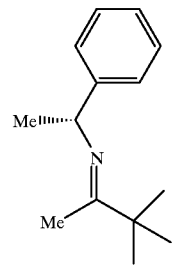

as a colorless oil. This material was dissolved in anhydrous THF (210 mL) and treated at 0–2° C. with borane-THF complex (1M, 206 mL, 206 mmol). The mixture was allowed to come to room temperature, stirred for 5 h and concentrated in vacuo. To the resulting oily residue was carefully added ethanol (300 mL), and the mixture was refluxed for 1 h and concentrated again in vacuo. The residue was chromatographed over basic alumina (activity grade 1/hexane) giving colorless oil. Proton NMR and HPLC (YMC C18 S3 4.6×50 mm column/water-MeOH—H$_3$PO$_4$ 90:10:0.2 to 10:90:0.2 gradient) indicated that this material was contaminated with ca. 10% of the (S,R)-diastereomer. Therefore, this mixture was resubjected to flash chromatography (silica gel/hexane-EtoAc-triethylamine 95:5:0.1) to afford

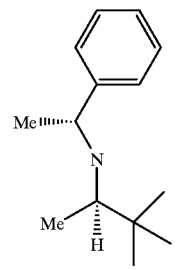

(11.45 g, 55.8 mmol, 54% yield). The above compound (11.45 g) and 10% palladium on carbon (1.5 g) were taken in EtOH (230 mL) and stirred under hydrogen for 12 hours. The mixture was filtered and the filtrate (ca. 230 mL) containing the title product was used as such for the next step as a ca. 0.24 M solution in ethanol (assumed 100% yield).

B. N-Cyano-N'-(4-cyanophenyl)thiourea, monosodium salt

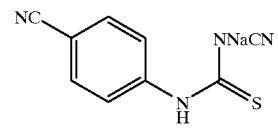

The title compound was prepared according to Example 1 Part A of U.S. Pat. No. 5,011,837.

C. (R)-4-[[(Cyanoimino)[(1,2,2-trimethyl-propyl)amino] methyl]amino]benzonitrile

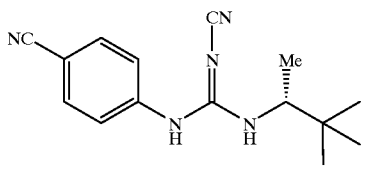

To a solution of Part B compound (6.0 g, 26.8 mmol) in DMF (150 mL) was sequentially added the solution of Part compound (ca. 0.24 M in EtOH, 112 mL, 26.8 mmol) and 1-(3-dimethylamino-propyl)-3-ethylcarbodiimide hydrochloride (WSC) (6.0 g, 31.3 mmol). The mixture was stirred at room temperature for 3 hours, diluted with ethyl acetate and sequentially washed with 1N HCl, water and brine. The organic layer was dried over magnesium sulfate, concentrated and the crude product was purified by flash chromatography on silica gel (hexanes-ethyl acetate-triethylamine 75:25:0.2) to afford a colorless foam. This material was recrystallized from isopropanol to give the title compound as a white solid (4.15 g, 57.6%), mp 159–60° C.; [a]XD –180° C.=1, MeOH; enantiomeric purity determined by chiral HPLC=99% (ChiralPak AD column/hexane-isopropanol-triethylamine 80:20:0.2); MS: 270 (M+H)$^+$; $^1$H NMR (CDCl$_3$) δ 8.65 (br s, 1H), 7.69 (d, 2H, J=8.79 Hz), 7.37 (d, 2H, J=8.79 Hz), 4.93 (br d, 1H), 3.83 (m, 1H), 1.10 (d, 1H, J=6.45 Hz), 0.90 (s, 9H).

Elemental analysis: calculated for $C_{15}H_{19}N_5$: C, 66.89; H, 7.11; N, 26.00 Found: C, 66.71; H, 7.14; N, 25.98.

EXAMPLE 2

(S)-4-[[(Cyanoimino)[(1,2,2-trimethylpropyl)amino]-methyl]amino]benzonitrile

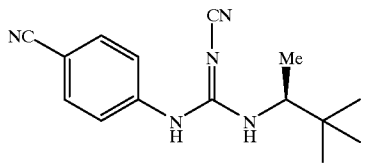

The title compound was prepared from Part B compound of Example 1 and (S)-1,2,2-trimethylpropyl amine (prepared according to Manley and Quast, *J. Med. Chem.*, 1992, 35, 2327–2340) by the same procedure as described in Example 1, Part C. The product was obtained as a colorless solid, mp 158–59° C.; [α]$_D$+189° C.=1, MeOH; enantiomeric purity determined by chiral HPLC=99.4% (ChiralPak AD column/hexane-isopropanol-triethylamine 80:20:0.2); MS: 270 (M+H)$^+$; $^1$H NMR (CDCl$_3$) δ 8.43 (br s, 1H), 7.69 (d, 2H, J=8.79 Hz), 7.37 (d, 2H, J=8.79 Hz), 4.93 (br d, 1H), 3.83 (m, 1H), 1.10 (d, 1H, J=6.45 Hz), 0.90 (s, 9H).

EXAMPLE 3

Comparison of Example 1-(R)-Enantiomer and Example 2-(S)-Enantiomer Re Hair Growth in an Animal Model The objective of the following described experiment was to compare and evaluate the in vivo effect of the Example 1-(R)-enantiomer and the Example 2-(S)-enantiomer on hair growth in an animal model. The two enantiomers were compared topically for hair growth in C3H mice.

Animal Model

The C3H mouse is a useful model for studying hair growth. Its usefulness rests with the fact that skin pigmentation of this animal is provided by the melanocytes of the hair follicle and not the epidermis. In the telogen or the resting phase of the hair follicle, the skin is pink. In the earliest phase of anagen or the growth phase, there is sudden graying of the skin and as the anagen phase progresses the skin becomes darker in color. In this study, visual observation was used as an in vivo assay of anagen induction. Furthermore as anagen develops, the skin thickness increases from a thin telogen skin to a measurably thickened anagen skin. Thus, recording the skin color and microscopic thickness of skin from these mice offers a sensitive, quantifiable and convenient method of assessing the phases of hair growth.

Groups of 20, six to seven week old male C3H mice with hair follicles in the resting phase of hair growth were used. At this stage in their life, the hair follicles remain in the telogen phase for up to 30 days or longer. This provides an adequate window of time to screen drugs. Compounds that improve hair growth stimulate the hair follicles from the telogen to the anagen phase. This stimulation is manifested by the shortening of the telogen phase of the hair follicle cycle.

Animals were anesthetized with ketamine/rompun (100 mg/Kg and 12 mg/Kg) IP and the hair over a defined dorsal area were closely clipped.

Animals with pink skin were treated topically 1× daily, 5 days per week with 50 microliters of a 2% solution of Example 1-(R)-enantiomer and a 2% solution of Example 1-(S)-enantiomer or vehicle by itself, applied to the dorsal area. The vehicle employed was ethanol/propylene glycol/water, 60/30/10. Treatment was continued for at least 4–5 weeks.

Animals were observed daily for side effects and changes to the test sites. All observations were documented. Test sites were graded weekly for changes in skin color and hair growth. In this study drug effects were evaluated using the visual observation of skin changing from pink to gray and resulting in hair growth.

Results

The percent of animals that induced hair follicle stimulation during the treatment period is illustrated in the accompanying Figure below. The most significant observation made between the two enantiomers is the difference in the time of onset of follicle stimulation. The time of onset for the Example 1-(R)-enantiomer was day 7 compared to day 11 for Example 2-(S)-enantiomer. The time of onset for the vehicle control was day 28. By day 11 of treatment the Example 1-(R)-enantiomer caused hair follicle stimulation in 40% of the test mice compared to only 5% with Example 2-(S)-enantiomer. By day 14, 50% of the animals treated with Example 1-(R)-enantiomer showed hair follicle stimulation compared to 25% for Example 2-(S)-enantiomer. By day 28, 85% of the animals treated with the Example 1-(R)-enantiomer showed hair follicle stimulation as compared to 65% treated with Example 2-(S)-enantiomer. Thus throughout the treatment period, the group treated with Example 1-(R)-enantiomer showed a higher incidence of hair follicle stimulation as compared to the group treated with Example 2-(S)-enantiomer.

The attached Figure shows the effect of 1× daily topical application of Example 1-(R)-enantiomer and Example 2-(S)-enantiomer.

In conclusion, these results in the C3H mice indicate that there is a remarkable difference between the Example 1-(R)-enantiomer and the Example 2-(S)enantiomer in their effect on hair follicle stimulation; in particular the (R)-enantiomer has a faster onset of action compared to the corresponding (S)-enantiomer.

These results are indeed surprising and unexpected especially in view of the vasorelaxant potencies of each of these enantiomers, which is generally recognized as an indication of hair growth promoting properties (Side Effects of Vasodilator Therapy, W. A. Pettinger et al, Hypertension, 1988, Vol. 11, II-34 to II-36, and Minoxidil Stimulates Cutaneous Blood Flow in Human Balding Scalps: Pharmacodynamics measured by laser Doppler velocimetry and photopulse plethysmography. R. C. Wester et al, J. Invest. Dermatol., 184, Vol. 82, 515–517).

Thus, while the $IC_{50}$ for vasorelaxant potency of the (R)-enantiomer is 47±17 nM versus 157±35 nM for the (S)-enantiomer, as seen above, the hair growth promoting ability of the (R)-enantiomer for producing hair growth within 11 days of treatment is 8 times greater than the corresponding (S)-enantiomer.

What is claimed is:

1. A formulation for promoting hair growth comprising the (R)-enantiomer of 4-[[(cyanoimino)[(1,2,2-trimethylpropyl)amino]methyl]amino]benzonitrile having the structure

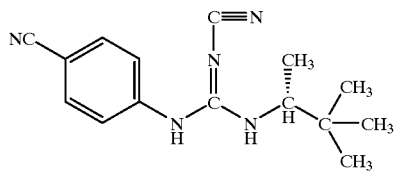

or a pharmaceutically acceptable salt thereof, and a pharmaceutically acceptable carrier therefor comprising ethanol, propylene glycol and water in a 60/30/10 proportion.

2. The formulation as defined in claim 1 comprising from about 0.01 to about 15% by weight of said (R)-enantiomer.

3. The formulation as defined in claim 1 comprising from about 0.1 to about 10% by weight of said (R)-enantiomer.

4. The formulation as defined in claim 1 comprising a 2% solution of said (R)-enantiomer.

5. A topical formulation for promoting hair growth comprising the (R)-enantiomer of 4-[[(cyanoimino)-[(1,2,2-trimethylpropyl)amino]methyl]-amino]benzonitrile having the structure

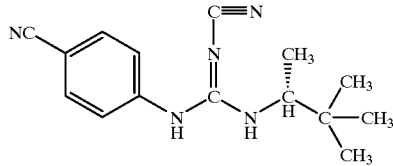

or a pharmaceutically acceptable salt thereof, and a pharmaceutically acceptable carrier therefor comprising ethanol/propylene glycol/water, 60/30/10, in an amount to provide a 2% solution of the (R)-enantiomer.

6. The formulation as defined in claim 1 wherein the (R)-enantiomer is substantially separated from its corresponding (S)-enantiomer.

7. The formulation as defined in claim 1 wherein the (R)enantiomer is in substantially pure form.

8. The formulation as defined in claim 1 wherein the (R)-enantiomer has an enantiomeric purity equal to at least 99%.

9. The formulation as defined in claim 1 which includes one or more other hair growth promoting agents.

10. The formulation as defined in claim 9 wherein said other hair growth promoting agent is selected from the group consisting of another potassium channel opener, a 5-α-reductase inhibitor, an androgen blocker, betamethasone dipropionate, a corticosteroid, scopolamine or cyproterone acetate or a mixture thereof.

11. The formulation as defined in claim 10 wherein the other potassium channel opener is minoxidil, diazoxide, cromakalim or pinacidil or a mixture thereof; the 5-α-reductase inhibitor is selected from the group consisting of finasteride, terazosin HCl, or doxaosin mesylate or a mixture thereof; the androgen blocker is 4-(5-methoxyheptyl)-hexahydro-2(1H)-pentalenone; and the corticosteroid is hydrocortisone.

12. The formulation as defined in claim 10 wherein said other hair growth promoting agent is a 5-α-reductase inhibitor.

13. The formulation as defined in claim 12 wherein the 5-α-reductase inhibitor is finasteride.

14. A method for promoting hair growth which comprises administering to a human in need of treatment a formulation for promoting hair growth comprising a therapeutically effective amount of the formulation as defined in claim 1.

15. The method as defined in claim 14 wherein the (R)-enantiomer is administered topically.

16. The method as defined in claim 14 wherein said formulation comprises from about 0.01 to about 15% by weight of said (R)-enantiomer.

17. The method as defined in claim 14 wherein said formulation comprises from about 0.1 to about 10% by weight of said (R)-enantiomer.

18. The method as defined in claim 14 wherein said formulation comprises 2% by weight of said (R)-enantiomer.

19. The method as defined in claim 14 wherein said other hair growth promoting agent is another potassium channel opener, a 5-α-reductase inhibitor, an androgen blocker, betamethasone dipropionate, a corticosteroid, scopolamine and/or cyproterone acetate.

20. The method as defined in claim 19 wherein the other potassium channel opener is minoxidil, diazoxide, cromakalim and/or pinacidil; the 5-α-reductase inhibitor is finasteride, terazosin HCl, and/or doxaosin mesylate; the androgen blocker is 4-(5-methoxyheptyl)-hexahydro-2(1H)-pentalenone, and the corticosteroid is hydrocortisone.

21. The method as defined in claim 14 wherein said other hair growth promoting agent is a 5-α-reductase inhibitor.

22. The method as defined in claim 21 wherein the 5-α-reductase inhibitor is finasteride.

23. A method for promoting hair growth which comprises topically administering to a human in need of treatment a formulation for promoting hair growth comprising a therapeutically effective amount of the (R)-enantiomer of 4-[[cyanoimino)[(1,2,2-trimethylpropyl)-amino]methyl]-amino]benzonitrile having the structure

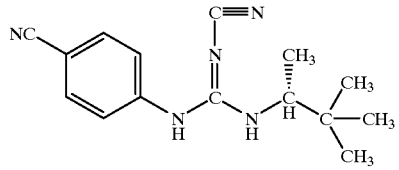

or a pharmaceutically acceptable salt thereof, and a pharmaceutically acceptable carrier therefor comprising ethanol/propylene glycol/water, 60/30/10, in an amount to provide a 2% solution of the (R)-enantiomer.

* * * * *